United States Patent
Labadie et al.

(10) Patent No.: US 7,981,122 B2
(45) Date of Patent: Jul. 19, 2011

(54) ADJUSTABLE SURGICAL PLATFORM AND SURGICAL INSTRUMENT USING SAME

(75) Inventors: Robert F. Labadie, Nashville, TN (US); J. Michael Fitzpatrick, Nashville, TN (US); Jason E. Mitchell, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 51 days.

(21) Appl. No.: 11/782,305

(22) Filed: Jul. 24, 2007

(65) Prior Publication Data

US 2008/0027463 A1 Jan. 31, 2008

Related U.S. Application Data

(60) Provisional application No. 60/832,776, filed on Jul. 24, 2006.

(51) Int. Cl.
*A61B 19/00* (2006.01)

(52) U.S. Cl. ............................ 606/130; 606/96; 248/168

(58) Field of Classification Search ................... 606/130, 606/172, 80, 96; 248/168, 405
See application file for complete search history.

(56) References Cited

U.S. PATENT DOCUMENTS

| | | | | |
|---|---|---|---|---|
| 3,881,675 A | * | 5/1975 | Matchett | 248/170 |
| 4,613,324 A | * | 9/1986 | Ghajar | 604/539 |
| 4,821,716 A | * | 4/1989 | Ghajar et al. | 606/172 |
| 6,579,281 B2 | * | 6/2003 | Palmer et al. | 606/1 |
| 6,893,447 B2 | * | 5/2005 | Dominguez et al. | 606/130 |
| 2005/0119639 A1 | * | 6/2005 | McCombs et al. | 606/1 |
| 2006/0086868 A1 | * | 4/2006 | White | 248/163.1 |
| 2007/0106305 A1 | * | 5/2007 | Kao et al. | 606/130 |
| 2007/0191852 A1 | * | 8/2007 | Shimko et al. | 606/79 |

* cited by examiner

*Primary Examiner* — Gary Jackson
*Assistant Examiner* — Katherine M Dowe
(74) *Attorney, Agent, or Firm* — Morris Manning Martin LLP; Tim Tingkang Xia, Esq.

(57) ABSTRACT

In one aspect, the present invention relates to a surgical instrument for providing an access to a target of interest of a living subject. In one embodiment, the surgical instrument has a bearing member, a shaft member and a probe. The bearing member has a first end portion, an opposite, second end portion, a body portion defined therebetween having a longitudinal axis, and a shoulder portion extending from the second end portion. The body portion defines a bore therein along the longitudinal axis. The shoulder portion defines a passage substantially coaxial with and in communication with the bore. The shaft member has an first end portion and an opposite, second end portion, and is slidably received in the bore of the bearing member. The shaft member defines a space extending from the first end portion to the second end portion. The probe has a working end portion and is received in the space of the shaft member such that the working end portion is extendable through the passage of the shoulder portion of the bearing member to reach a target of interest of a living subject so as to provide an access thereto.

13 Claims, 16 Drawing Sheets

ADJUSTABLE SURGICAL PLATFORM AND SURGICAL INSTRUMENT USING SAME

CROSS-REFERENCE TO RELATED PATENT APPLICATION

This application claims the benefit, pursuant to 35 U.S.C. §119(e), of U.S. provisional patent application Ser. No. 60/832,776, filed Jul. 24, 2006, entitled "Adjustable Surgical Platform, Surgical Instrument, System and Methods of Making and Using Same," by Robert F. Labadie, and J. Michael Fitzpatrick, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT OF FEDERALLY-SPONSORED RESEARCH

This invention was made with government support under Contract No. R21 2886awarded by the National Institute of Biomedical Imaging and Bioengineering of the National Institutes of Health. The government has certain rights in this invention.

FIELD OF THE INVENTION

The present invention generally relates to a surgical instrument. More particularly, the present invention relates to a surgical instrument associated with a surgical platform that has one or more adjustable support members.

BACKGROUND OF THE INVENTION

The therapies of deep-brain stimulation (DBS) and auditory neuron stimulation have gained significantly clinical popularity over the past decades. The former has significant applications in the treatment of a variety of brain-controlled disorders, including movement disorders, while the latter has applications in the treatment of hearing impairment.

Generally, such treatments involve identifying a corresponding physiological target to be stimulated, surgically drilling a burr hole in the patient's skull or temporal bone to create an access to the corresponding physiological target, placing an electronic device in the corresponding physiological target through the drilled burr hole, and then applying appropriate stimulation signals through the implanted electrode device to the physiological target.

The placement portion of the treatment, involving stereotactic neurosurgical methodology, is very critical, and has been the subject of much attention and research. In particular, finding the deep brain target and then permanently placing the electrode lead so that it efficiently stimulates such target is very important.

Stereotactic neurosurgery is a field of neurosurgery in which a probe is advanced through a burr hole to a target of interest by means of a mechanical device attached to the skull with aiming based on pre-operative images. The probe may be a biopsy needle or an implantable device, but it is geometrically rigid, so that its tip, or working end portion, can be brought to a target of interest specified on a pre-operative image, by means of a geometrical calculation. For the past decade, the field has been advancing from the imposition of large, classical metal frames, which encompass the entire head of a patient, to the attachment of small platforms placed only over an entry site to reduce patient discomfort, facilitate surgical access, allow multiple targeting during one surgery via multiple platforms, and reduce procedure time, while maintaining the same level of accuracy.

Classical metal frames are designed for approaching one target at a time with an unrestricted entry point towards the deep target by employing the principle that the target is at the center of a sphere. Because of the long trajectories experienced by the probe when it goes through from a starting point, which is normally outside of the head of the patient, to target areas deep inside the head of the patient, both accuracy and patient comfort are challenged by the demands of surgeries for deep brain stimulation (DBS) in which the patients are awake throughout the lengthy surgery procedure (normally about 5-8 hours).

During the last few years, microplatforms, such as a NEXFRAME™ (Image-Guided Neurologics, Inc, Melbourne, Fla.) and a microtargeting platform (FHC Inc, Bowdoinham, Me.), also known as a STarFix™ platform, have become available as replacements for the classical frames for DBS stereotactic surgery.

It is understood that the NEXFRAME™ platform requires the attachment of bone-implanted fiducials, the subsequent acquisition of a preoperative tomogram, and intraoperative optical tracking to aim a probe at its target. However, there are problems regarding geometrically stability, limited space for access to the burr hole and surgical manipulation once the tower is mounted, the time consuming process of aiming, and the difficulty of locking on the target. Access to the burr hole is crucially important for the purpose of stopping bleeding from the bone cavity, dura, and the surface of the cortex during the procedure. Aiming is achieved by watching a guiding icon on the screen of the intraoperative tracking system, while adjusting the orientation of the platform. When the icon indicates a correct trajectory, the platform must be locked into place with one hand, while it is held at the correct trajectory with the other. The trajectory is two-dimensional, meaning that there are two mutually perpendicular angular adjustments required, each of which must be set simultaneously for the correct trajectory. Finding the correct trajectory via the guiding icon is time consuming because of the difficulty of making fine adjustments of one angle of the approach without changing the other angle. A further difficulty with this aiming procedure is maintaining both angles of the correct trajectory while locking the device on target. The locking step can be especially frustrating, because, if either angle is changed inadvertently during locking, as revealed by the guiding icon, the device must be unlocked and the adjustment started from the beginning. Typically several iterations are required, resulting in wasted operating time.

It is understood the other alternative, the STarFix™, also requires the attachment of bone-implanted fiducials and the subsequent acquisition of a preoperative tomogram, but it does not require intraoperative optical tracking for aiming. Instead the STarFix™ is custom-made for each patient based on a pre-operative tomogram and the surgeon's identification of the entry point and the target on that tomogram. The device arrives at the operating suite pre-aimed with no adjustment required intraoperatively. It is a one-piece rigid plastic block having a cylindrical hole that accommodates the probe, supported by a plurality of legs, each of which attaches to a base that is implanted in the skull. Fiducial markers are attached to these same bases before the pre-operative image is acquired and discarded after imaging. The shape of the STarFix™ provides far greater access to the burr hole, but its paramount advantage is that it is "pre-aimed", obviating the aiming procedure required by the NEXFRAME™. An additional benefit, but one that does not directly affect accuracy or operating time is that the expense of an intraoperative tracking system is avoided. One of its disadvantages relative to the NEXFRAME™ is that the patient must wait between the acquisition of the tomogram and the delivery of the STarFix™. Currently, this interval ranges from two to four days. The wait between image acquisition and surgery is a disadvantage inherent to the production of the customized STarFix™, but the primary disadvantages of the NEXFRAME™ are a consequence only of its mechanical design.

Therefore, a heretofore unaddressed need still exists in the art to address the aforementioned deficiencies and inadequacies.

SUMMARY OF THE INVENTION

The present invention, in one aspect, relates to a surgical instrument for providing an access to a target of interest of a living subject. In one embodiment, the surgical instrument includes a bearing member, a shaft member, a guiding member, a probe and a platform.

The bearing member has a first end portion, an opposite, second end portion, a body portion defined therebetween having a longitudinal axis, and a shoulder portion extending from the second end portion. The body portion defines a bore therein along the longitudinal axis, and the shoulder portion defines a passage substantially coaxial with and in communication with the bore. In one embodiment, the shoulder portion has a step portion and a mouth portion extending from the step portion. In operation, the step portion of the shoulder portion of the bearing member is abutted against the base portion of the platform.

The guiding member has a groove formed thereon and extending longitudinally from the exterior surface of the guiding member. The guiding member is received in the bore and positioned against the shoulder portion of the bearing member.

The shaft member has a first end portion, an opposite, second end portion, and a body portion defined therebetween, which defines a space therein extending from the first end portion to the second end portion. The shaft member is slidably received in the bore of the bearing member. In one embodiment, the shaft member further has a guide rail extending longitudinally from the exterior surface of the shaft member, which is engagable with the groove of the guiding member such that the shaft member is slidable in the bore of the bearing member along the longitudinal axis of the bore of the bearing member.

The probe has a working end portion and is received in the space of the shaft member such that the working end portion is substantially coaxial with and extendable through the passage of the bearing member to reach the target of interest of the living subject. In one embodiment, the probe includes a surgical drill, and the working end portion is the tip portion of the surgical drill.

The platform is adapted for receiving the shoulder portion of the bearing member and positioning the working end portion of the probe towards the target of interest of the living subject along a planned trajectory so as to provide an access thereto.

In one embodiment, the platform has a base portion and a plurality of supporting legs extending from the base portion. The base portion defines an opening for receiving the shoulder portion of the bearing member therein. Each of the plurality of supporting legs has a length that is different from or substantially identical to each other. When the shoulder portion of the bearing member is received in the base portion, the working end portion of the probe is positioned towards the target of interest of the living subject along the planned trajectory. In one embodiment, the length of each of the plurality of supporting legs is fixed. In another embodiment, the length of at least one of the plurality of supporting legs is adjustable.

The shaft member is encircled substantially by a collar portion at the first end portion of the shaft member.

The surgical instrument further includes a drive mechanism for driving the probe so as to provide the access to the target of interest of the living subject.

In another aspect, the present invention relates to a surgical instrument for providing an access to a target of interest of a living subject. In one embodiment, the surgical instrument includes a bearing member having a first end portion, an opposite, second end portion, a body portion defined therebetween and having a longitudinal axis, and a shoulder portion extending from the second end portion. The body portion defines a bore therein along the longitudinal axis. The shoulder portion defines a passage substantially coaxial with and in communication with the bore.

Furthermore, the surgical instrument includes a shaft member having an first end portion and an opposite, second end portion, slidably received in the bore of the bearing member, where the shaft member defines a space extending from the first end portion to the second end portion.

The surgical instrument also includes a probe having a working end portion, received in the space of the shaft member such that the working end portion is extendable through the passage of the shoulder portion of the bearing member. In operation, the working end portion of the probe is substantially coaxial with the passage of the shoulder portion of the bearing member. In one embodiment, the probe includes a surgical drill.

The surgical instrument may further include a platform for receiving the shoulder portion of the bearing member and positioning the working end portion of the probe towards the target of interest of the living subject along a planned trajectory.

Additionally, the surgical instrument may include a drive mechanism for driving the probe so as to provide the access to the target of interest of the living subject.

In yet another aspect, the present invention relates to a surgical instrument for providing an access to a target of interest of a living subject. In one embodiment, the surgical instrument has a bearing member having a first end portion, an opposite, second end portion, and a body portion defined therebetween and forming a bore therein along a longitudinal axis, a first bearing and a second bearing. The bore is formed between the first bearing and the second bearing and substantially at the center of the body portion.

Furthermore, the surgical instrument has a first shaft member and a second shaft member that are received in the first bearing and the second bearing of the bearing member, respectively. Each shaft member has a first end portion, an opposite, second end portion), and a body portion defined therebetween.

Moreover, the surgical instrument has a mounting member having a first surface, an opposite, second surface, a body portion defined therebetween, a shoulder portion extending from the second surface, a passage formed through the body portion and the shoulder portion, and a first recess and a second recess formed on the first surface. As assembled, the second end portions of the first shaft member and the second shaft member are received in and mounted to the first recess and the second recess of the collar member, respectively, and the passage of the collar member is substantially coaxial with the bore.

The surgical instrument further has a collar member having a first surface, an opposite, second surface, a body portion defined therebetween forming a passage therein extending from the center of the first surface to the center of the second surface, and a first recess and a second recess formed on the second surface. As assembled, the first end portions of the first shaft member and the second shaft member are received in and mounted to the first recess and the second recess, respectively. The passage is substantially coaxial with the bore of the bearing member.

Additionally, the surgical instrument has a probe having a working end portion, and is received in the bore of the bearing member such that the working end portion is substantially coaxial with and extendable through the passage of the mount member to the target of interest of the living subject. In one embodiment, the probe includes a surgical drill.

The surgical instrument also has a platform for receiving the mounting member and positioning the working end portion of the probe towards the target of interest of the living subject along a planned trajectory so as to provide an access thereto.

The platform comprises a base portion and a plurality of supporting legs extending from the base portion. In one embodiment, the base portion of the platform defines an opening for receiving the shoulder portion of the bearing member therein, and each of the plurality of supporting legs has a length that is different from or substantially identical to each other, such that when the shoulder portion of the bearing member is received in the base portion, the working end portion of the probe is positioned towards the target of interest of the living subject along the planned trajectory. In one embodiment, the length of each of the plurality of supporting legs is fixed. In another embodiment, the length of at least one of the plurality of supporting legs is adjustable.

The surgical instrument may also have a drive mechanism for driving the probe.

In a further aspect, the present invention relates to a surgical instrument for providing an access to a target of interest of a living subject. In one embodiment, the surgical instrument has a bearing member. The bearing member has a first end portion, an opposite, second end portion, and a body portion defined therebetween forming a bore therein along a longitudinal axis, a first bearing and a second bearing.

The surgical instrument further has a first shaft member and a second shaft member slidably received in the first bearing and the second bearing of the bearing member, respectively.

Moreover, the surgical instrument has a mounting member having a first surface, an opposite, second surface, a body portion defined therebetween forming a passage therein, and a first recess and a second recess formed on the first surface. As assembled, one end of the first shaft member and one end of the second shaft member are received in and mounted to the first recess and the second recess of the mounting member, respectively. The passage of the mounting member is substantially coaxial with the bore.

Additionally, the surgical instrument has a probe having a working end portion, received in the bore of the bearing member such that the working end portion is substantially coaxial with and extendable through the passage of the mounting member. In one embodiment, the probe includes a surgical drill.

The surgical instrument further has a platform for receiving the mounting member and positioning the working end portion of the probe towards the target of interest of the living subject along a planned trajectory.

The surgical instrument may also have a drive mechanism for driving the probe so as to provide the access to the target of interest of the living subject.

In yet a further aspect, the present invention relates to a surgical platform usable for engaging with a surgical instrument as to provide an access to a target of interest of a living subject. In one embodiment, the surgical platform includes a body portion having a first surface, an opposite, second surface, and a body portion defined therebetween, and a plurality of recesses formed on the second surface. The body portion defines a bore extending from the first surface to the second surface substantially along a longitudinal axis. The plurality of recesses is formed with dimensions that are different from or substantially identical to each other. In operation, the surgical instrument is received in the bore of the bearing member such that a working end portion of the surgical instrument is extendable through the bore to the target of interest of the living subject along the longitudinal axis, which is substantially coaxial with a planned trajectory.

Furthermore, the surgical platform has a plurality of mounting members. Each mounting member has a body portion defining a concave surface, and is received in a corresponding one of the plurality of recesses of the bearing member. The plurality of mounting members is different from or substantially identical to each other.

In one embodiment, the plurality of mounting members comprises a first mounting member, a second mounting member and a third mounting member. Each of the first mounting member, the second mounting member and the third mounting member has a body portion having a first surface and a second surface that is substantially convex, and a shaft portion extending from the body portion at the first surface. The body portion comprises an at least partially cylindrical body, or an at least partially spherical body.

Moreover, the surgical platform has a plurality of support members. Each support member is engaged with a corresponding one of the plurality of mounting members for supporting the body member. At least one of the plurality of support members is formed with an engagement portion that has a convex surface to be complimentarily received in the concave surface of a corresponding one of the plurality of mounting members. Each pair of the plurality of support members defines an adjustable relative position and orientation therebetween. When a relative position and orientation between a pair of the plurality of support members is adjusted, the relative orientation of the longitudinal axis to the planned trajectory is adjusted accordingly.

The plurality of support members is different from or substantially identical to each other.

In one embodiment, the plurality of support members has a first support member, a second support member and a third support member. Each of the first support member, the second support member and the third support member comprises a shaft portion having a first end portion and an opposite, second end portion, an engagement portion mounted to the first end portion of the shaft portion, and an end portion mounted to the second end portion of the shaft portion. In one embodiment, the shaft portion is formed with an outer threaded segment, and the engagement portion is formed with an outer convex surface and an inner cavity defined by an inner threaded segment adapted for movably engaging with the shaft portion through the corresponding outer threaded segment. An effective length of each support member is adjustable by rotating the engagement portion along the shaft portion. The engagement portion has a ball member and the outer convex surface comprises a substantially spherical surface. In one embodiment, the end portion comprises a mounting member adapted for engaging a fiducial marker in use. In another embodiment, the end portion comprises a magnetic member adapted for engaging a fiducial marker in use.

In one embodiment, each of the first mounting member, the second mounting member and the third mounting member further has an arm member projecting radially away from the second surface of a corresponding body portion.

The surgical platform may further have a plurality of engaging member means for mounting the plurality of mounting members to the body member through the plurality of recess, respectively.

In one aspect, the present invention relates to a surgical platform usable for engaging with a surgical instrument as to provide an access to a target of interest of a living subject. In one embodiment, the surgical platform includes a body member having a first surface, an opposite, second surface, a body portion defined therebetween, and a plurality of recesses formed on the second surface, where the body portion defines a bore extending from the first surface and the second surface substantially along a longitudinal axis for engaging with the surgical instrument. The surgical platform further includes a plurality of support members. Each support member is engagable with a corresponding one of the plurality of recesses of the body member for supporting the body member. In one embodiment, at least one of the plurality of recesses of the body member is formed with a concave surface. At least one of the plurality of support members is formed with an engagement portion that has a convex surface to be received in the concave surface of a corresponding at least one of the plurality of recesses. The convex surface of the engagement portion of the at least one of the plurality of support members is substantially complementary to the concave surface of the corresponding at least one of the plurality of recesses.

In operation, the surgical instrument is received in the bore of the body member such that a working end portion of the surgical instrument is extendable through the bore to the target of interest of the living subject along the longitudinal axis, which is substantially coaxial with a planned trajectory.

In one embodiment, each pair of the plurality of support members defines an adjustable relative position and orientation therebetween. When a relative position and orientation between a pair of the plurality of support members is adjusted, the relative orientation of the longitudinal axis to the planned trajectory is adjusted accordingly.

In one embodiment, the plurality of support members has a first support member, a second support member and a third support member. Each of the first support member, the second support member and the third support member comprises a shaft portion having a first end portion and an opposite second, end, an engagement portion mounted to the second end portion of the shaft portion, and an end portion mounted to the first end portion of the shaft portion. The shaft portion is formed with an outer threaded segment, and the engagement portion is formed with an outer convex surface and an inner cavity defined by an inner threaded segment adapted for movably engaging the shaft portion through the corresponding outer threaded segment. Accordingly, an effective length of the support member is adjustable by rotating the engagement portion along the shaft portion. The engagement portion comprises a ball member and the outer convex surface comprises a substantially spherical surface. In one embodiment, the end portion comprises a mounting member adapted for engaging a fiducial marker in use. In another embodiment, the end portion comprises a magnetic member adapted for engaging a fiducial marker in use.

In another aspect, the present invention relates to a surgical platform usable for engaging with a surgical instrument as to provide an access to a target of interest of a living subject. In one embodiment, the surgical platform includes a body member having a first surface, an opposite, second surface, a body portion defined therebetween, and a plurality of recesses formed on the second surface, where the body portion defines a bore extending from the first surface and the second surface substantially along a longitudinal axis for engaging with the surgical instrument.

Furthermore, the surgical platform includes a plurality of support members, each support member received in a corresponding one of the plurality of recesses for supporting the body member, having an effective length that is different from or substantially identical to each other, such that in operation, a working end portion of the surgical instrument is extendable through the bore to the target of interest of the living subject along the longitudinal axis that is aligned coaxially with a planned trajectory. In one embodiment, each pair of the plurality of support members defines an adjustable relative position and orientation therebetween. When a relative position and orientation between a pair of the plurality of support members is adjusted, the relative orientation of the longitudinal axis to the planned trajectory is adjusted accordingly. In one embodiment, the length of at least one of the plurality of supporting legs is adjustable. In another embodiment, the length of each of the plurality of supporting legs is fixed.

In one embodiment, at least one of the plurality of recesses is formed with a concave surface, and at least one of the plurality of support members is formed to have an engagement portion that has a convex surface to be received in the concave surface of a corresponding at least one of the plurality of recesses. The convex surface of the engagement portion of the at least one of the plurality of support members is substantially complementary to the concave surface of the corresponding at least one of the plurality of recesses.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
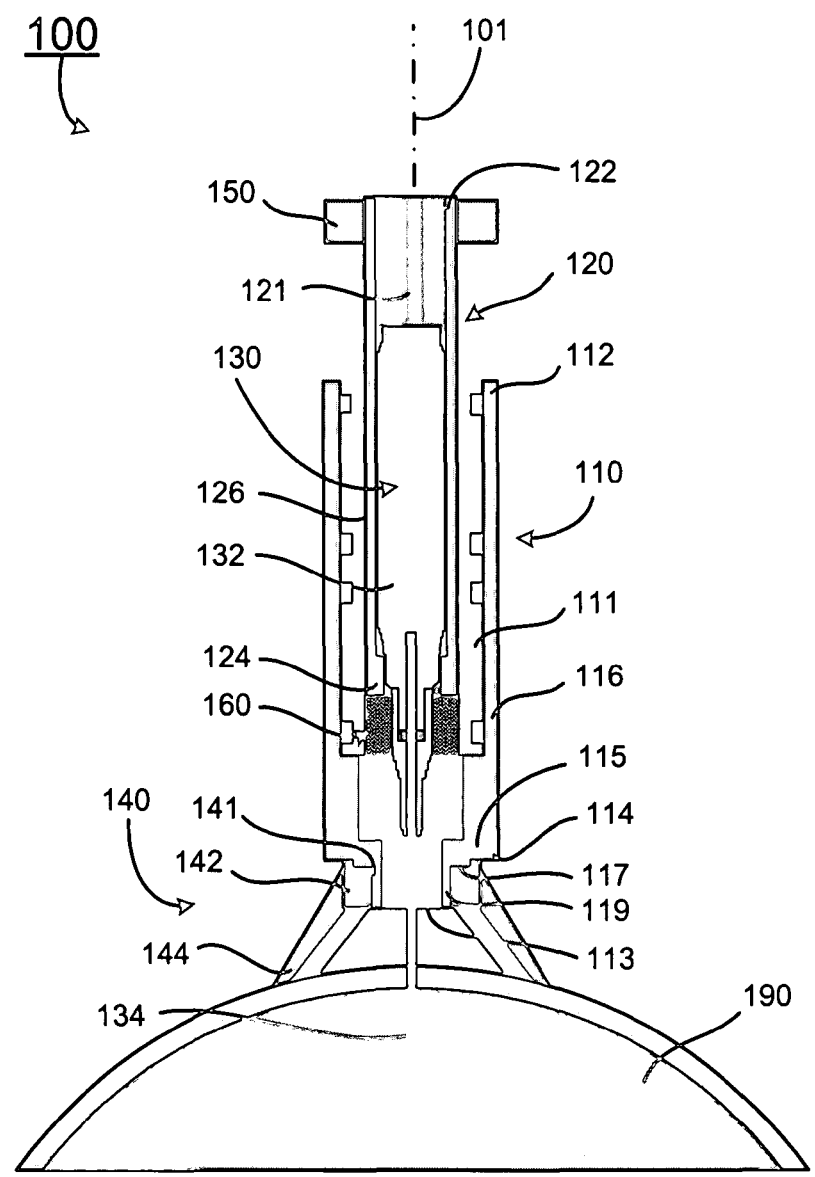
FIG. 1 shows a cross-sectional view of a surgical instrument according to one embodiment of the present invention associated with a surgical platform.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

Additionally, some terms used in this specification are more specifically defined below, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention. Additionally, certain theories are proposed and disclosed herein; however, in no way they, whether they are right or wrong, should limit the scope of the invention.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The description will be made as to the embodiments of the present invention in conjunction with the accompanying drawings of FIGS. 1-12. In accordance with the purposes of this invention, as embodied and broadly described herein, this invention, in one aspect, relates to a surgical instrument for providing an access to a target of interest of a living subject. The living subject can be a human or an animal. The target of interest can be areas in a deep brain, a middle ear or other anatomical structures of the living subject. The target of interest can also be areas in other body parts of a living subject.

Referring to FIGS. 1-4, and in particular to FIG. 1, the surgical instrument 100 according to one embodiment of the present invention is shown. The surgical instrument 100 includes a bearing member 110, a shaft member 120, a guiding member 160, a probe 130 and a platform 140.

The bearing member 110 has a first end portion 112, an opposite, second end portion 114, a body portion 116 defined therebetween along a longitudinal axis 101, and a shoulder portion 115 extending from the second end portion 114. The body portion 116 defines a bore 111 therein along the longitudinal axis 101. The shoulder portion 115 defines a passage 113 substantially coaxial with and in communication with the bore 111. Furthermore, the shoulder portion 115 has a step portion 117 and a mouth portion 119 extending from the step portion 117. In operation, the step portion 117 of the shoulder portion 115 of the bearing member 110 is abutted against the base portion 142 of the platform 140.

The guiding member 160 has a groove 168 formed thereon and extending longitudinally from the exterior surface of the guiding member 160. The guiding member 160 is received in the bore 111 and positioned against the shoulder portion 115 of the bearing member 110.

The shaft member 120 has a first end portion 122, an opposite, second end portion 124, and a body portion 126 defined therebetween. The body portion 126 defines a space 121 therein extending from the first end portion 122 to the second end portion 124. The shaft member 120 is slidably received in the bore 111 of the bearing member 110.

Figure 2:
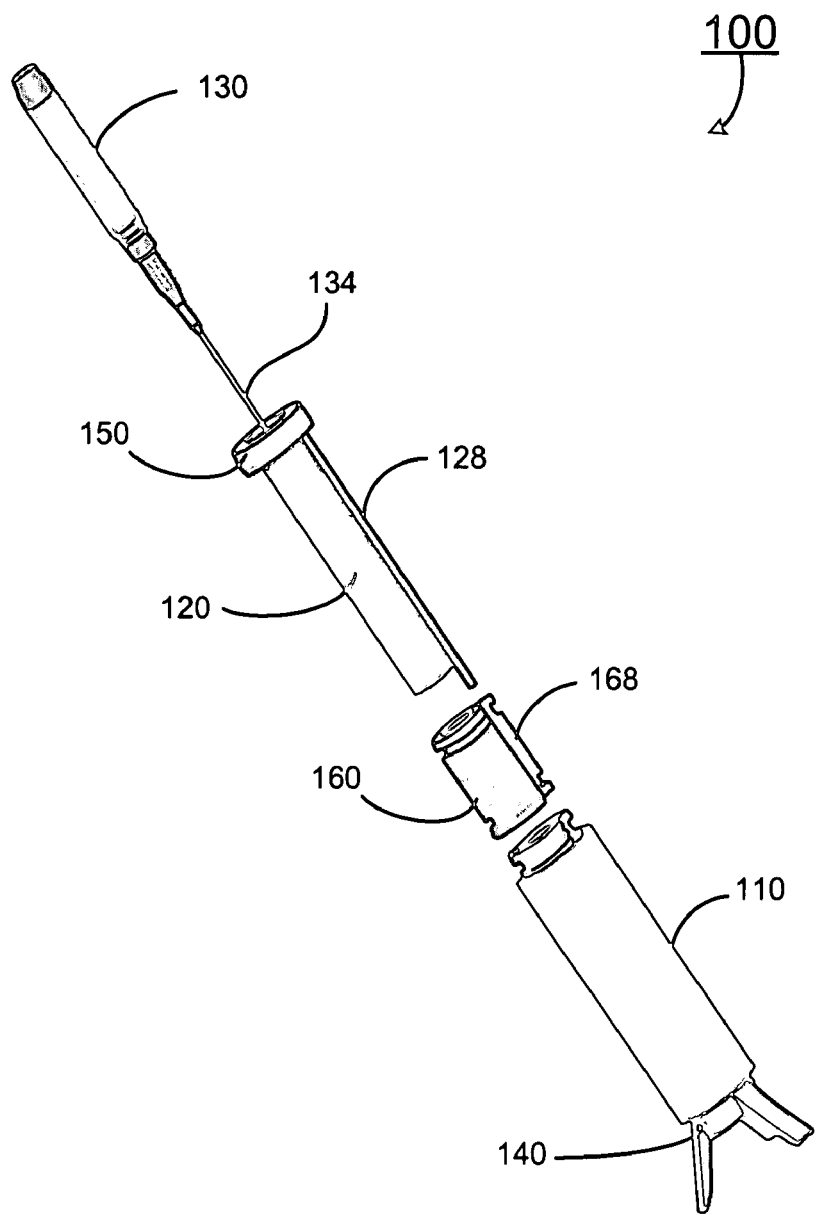
FIG. 2 shows an explosive view of the surgical instrument shown in FIG. 1.
Figure 3:
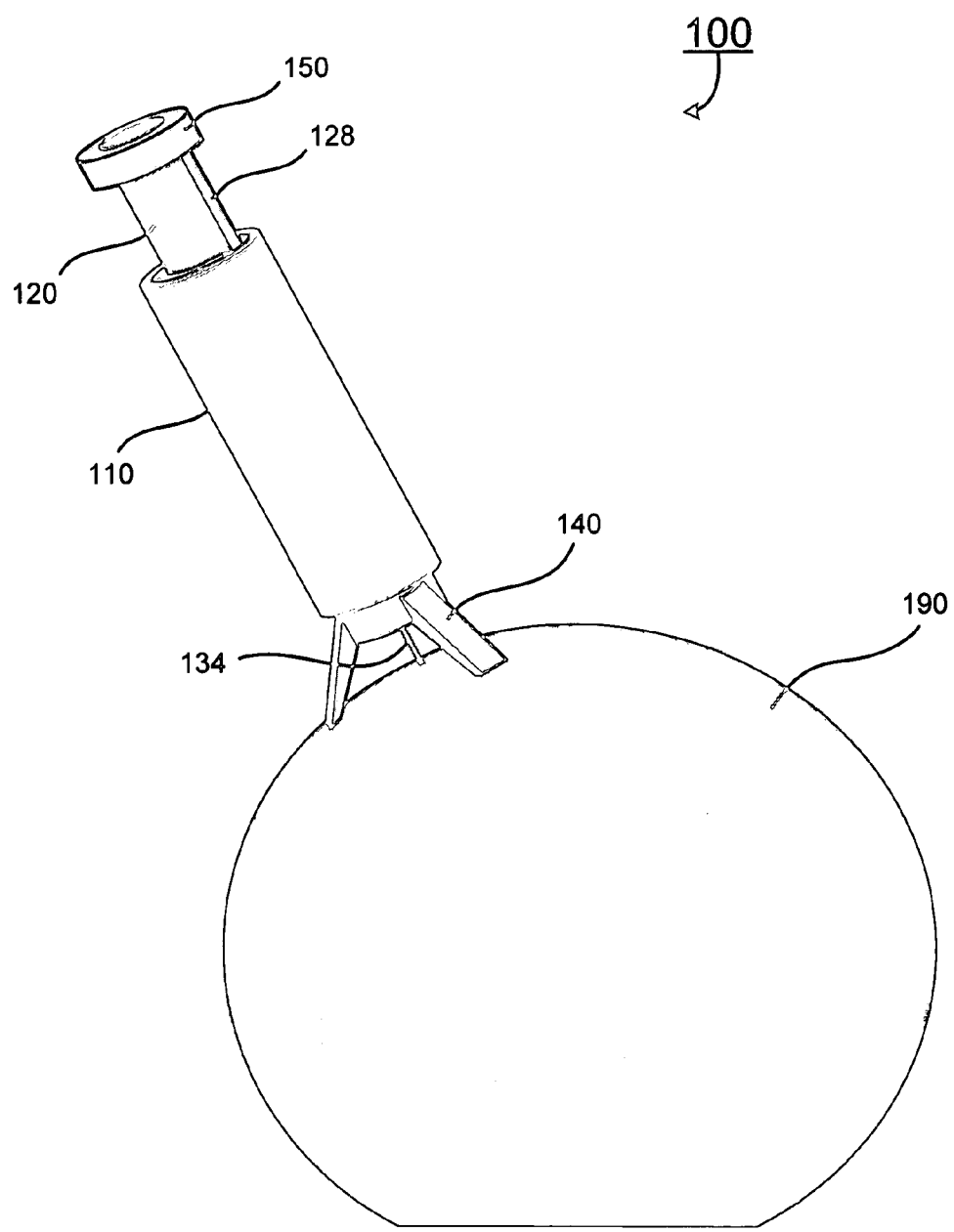
FIG. 3 shows a perspective view of the surgical instrument shown in FIG. 1.

As shown in FIG. 2, the shaft member 120 further has a guide rail 128 formed thereon and extending longitudinally from the exterior surface of the shaft member 120. The guide rail 128 is adapted for engaging with the groove 168 of the guiding member 160. As assembled, the shaft member 120 is slidable in the bore 111 of the bearing member 110 along the longitudinal axis 101 of the bearing member 110.

The shaft member 120 is encircled by a collar portion 150 substantially at the first end portion 122 of the shaft member 120.

The probe 130 has a body portion 132 and a working end portion 134 extending from the body portion 132. The probe 130, in operation, is received in the space 121 of the shaft member 120 such that the working end portion 134 is substantially coaxial with and extendable through the passage 113 of the shoulder portion 115 of the bearing member 110 to the target of interest of the living subject. In other words, the orientation and position of the working end portion 134 of the probe 130 is substantially coincident with the longitudinal axis 101 of the bearing member 110. The longitudinal axis 101 of the bearing member 110, thus the working end portion 134 of the probe 130, is preferably aligned to a planned trajectory that leads the working end portion 134 of the probe 130 to reach the target of interest of the living subject.

In practice, and as shown as an example in FIG. 2, the probe 130 can be a surgical drill. In this example, the working end portion 134 is the tip portion of the surgical drill Accordingly, the surgical instrument 100 can be used to drill a burr hole in the skull of a patient for the deep brain stimulation in the treatment of a variety of brain-controlled disorders, including movement disorders. The surgical instrument 100 can also be utilized to create an access to the middle ear of a patient in the treatment of hearing impairment. The probe 130 can also be a microelectrode recording lead, unipolar macrostimulation lead, or other types of stimulation devices.

Figure 4:
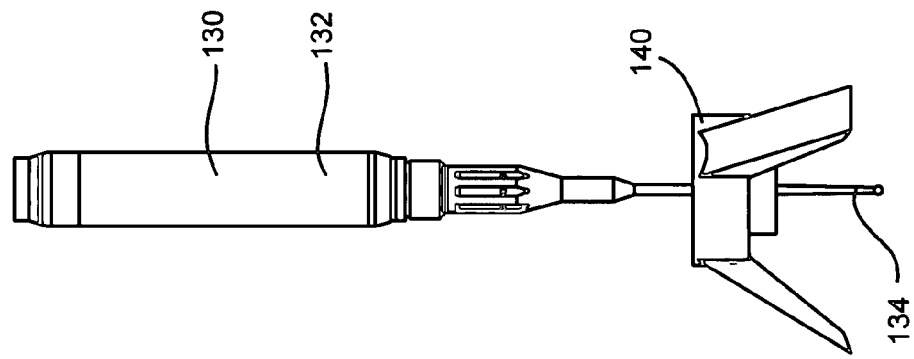
FIG. 4 shows a perspective view of a drill and a surgical platform associated with the surgical instrument shown in FIG. 1.
Figure 4:
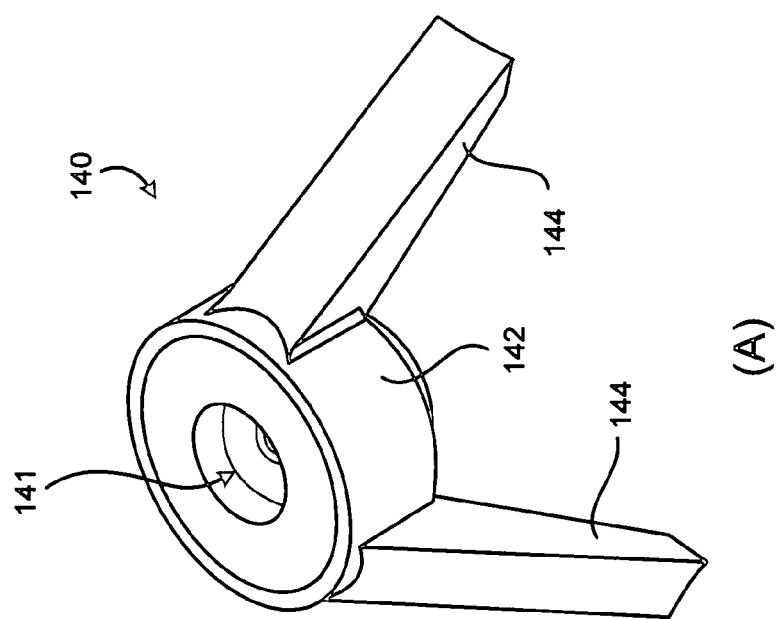

The platform 140 is adapted for receiving the shoulder portion 115 of the bearing member 110 and positioning the working end portion 134 of the drill 130 towards the target of interest of the living subject along the planned trajectory (not shown) so as to provide an access thereto. As shown in FIG. 4, the platform 140 has a base portion 142 and a plurality of supporting legs 144 extending from the base portion 142. The base portion 142 defines an opening 141 for receiving the shoulder portion 115 of the bearing member 110 therein. Each of the plurality of supporting legs 144 has a length. The length of each supporting leg 144 can be different from or substantially identical to each other. The platform 140, in operation, is secured to a region or area of interest 190 of the living subject in which the surgical procedures is performed.

The platform 140 can be a customized platform such as the STarFix™ platform where the length of each of three supporting legs is fixed. For the STarFix™ platform, it is uniquely manufactured based on a stereotactically planned trajectory for a specific patient, and the length of each supporting leg 144 is fixed. The platform 140 arrives at the operating suite pre-aimed with no adjustment required intra-operatively. When the shoulder portion 115 of the bearing member 110 is received in such a customized platform in operation, the working end portion 134 of the probe 130 is automatically aligned to the planned trajectory and positioned towards the target of interest of the living subject along the planned trajectory.

As described below, the length of at least one of the plurality of supporting legs 144 can also be adjustable. In this case, the working end portion 134 of the probe 130 can be intra-operatively aligned to the planned trajectory by adjusting the length of at least one of the plurality of supporting legs 144.

The surgical instrument 100 further includes a drive mechanism (not shown) for driving the probe 130 so as to provide the access to the target of interest of the living subject. For example, as known to people skilled in the art, the drive mechanism can include a motor and coupling means to electrically couple the motor to a source of electricity and to the probe 130 to drive the probe, respectively.

Figure 5:
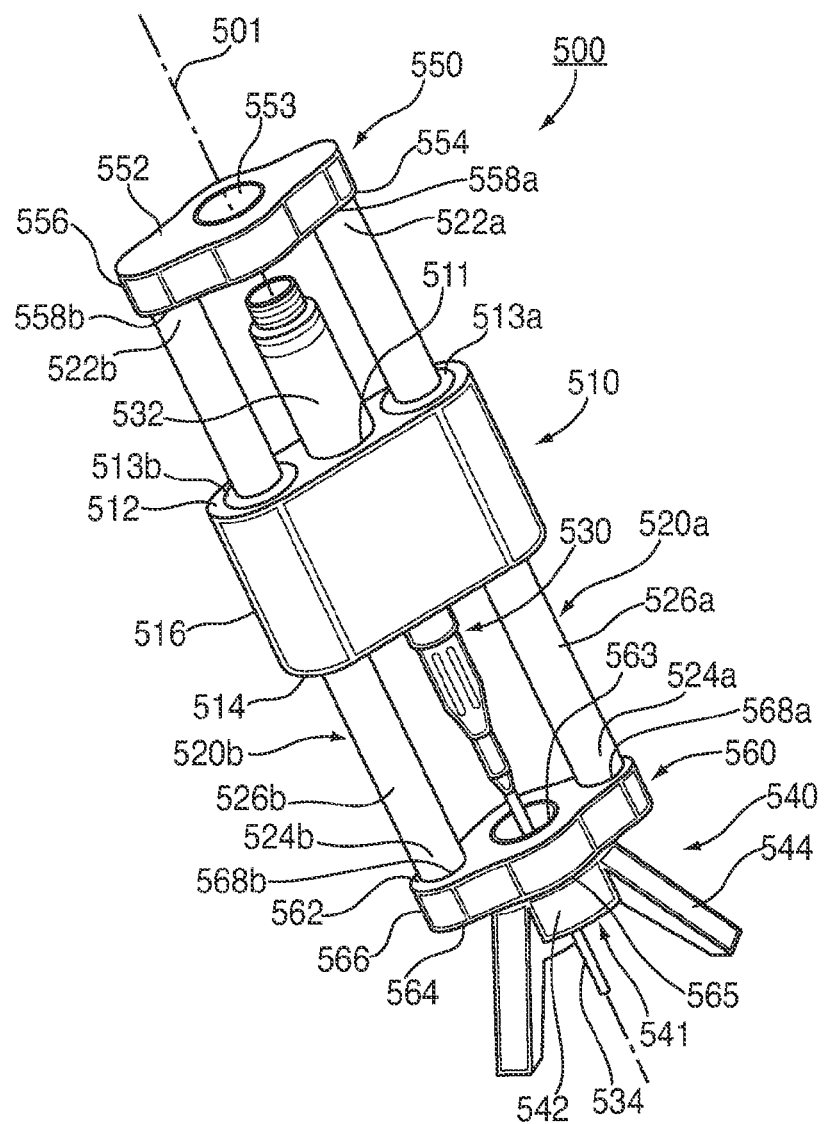
FIG. 5 shows a perspective view of a surgical instrument according to another embodiment of the present invention associated with a surgical platform.
Figure 6:
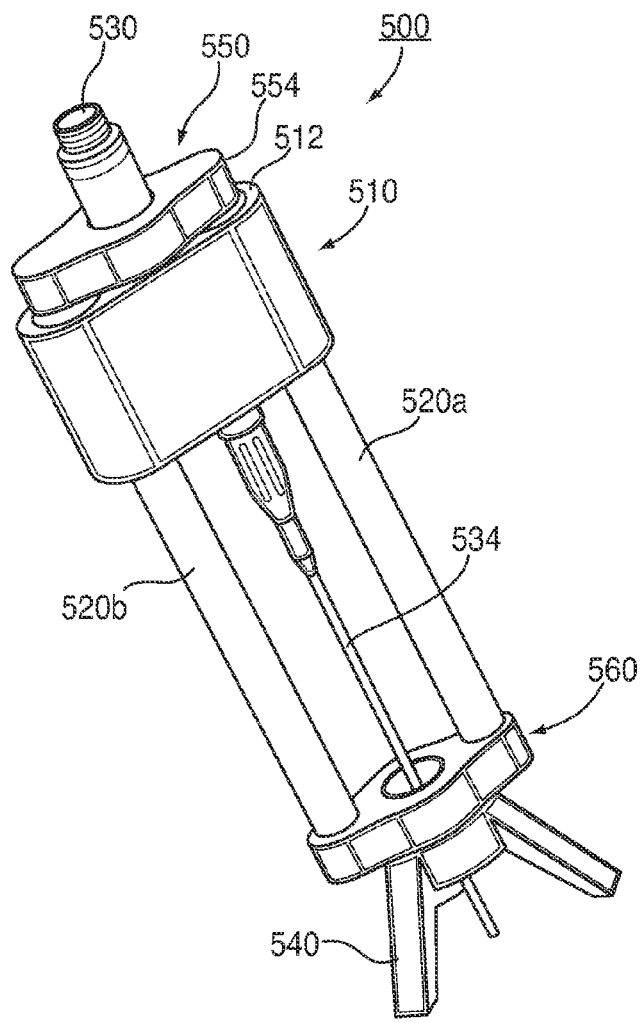
FIG. 6 shows a perspective view of the surgical instrument shown in FIG. 5 in a first position.
Figure 7:
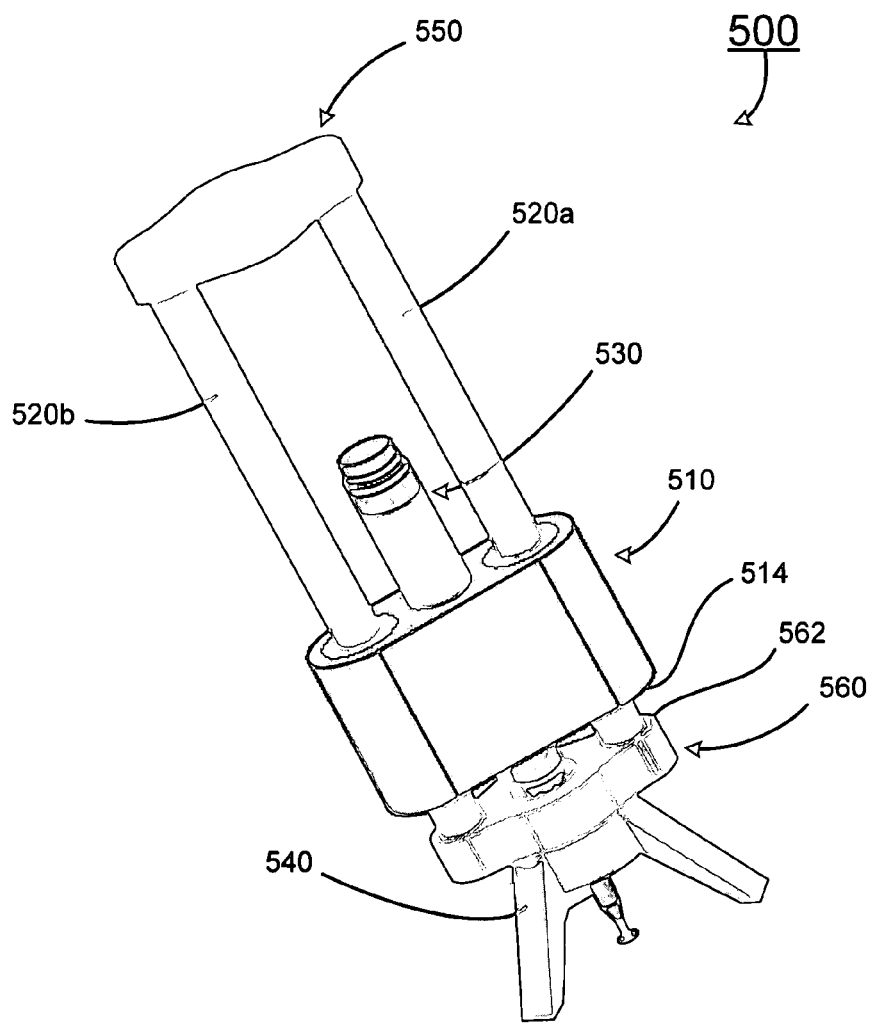
FIG. 7 shows a perspective view of the surgical instrument shown in FIG. 5 in a second position.

Referring to FIGS. 5-7, a surgical instrument 500 is shown according to another embodiment of the present invention. The surgical instrument 500 has a bearing member 510, a first shaft member 520a, a second shaft member 520b, a mounting member 560, a collar member 550, a probe 530 and a platform 540.

The bearing member 510 has a first end portion 512, an opposite, second end portion 514, a body portion 516 defined therebetween and forming a bore 511 therein along a longitudinal axis 501, a first bearing 513a and a second bearing 513b. The bore 511 is formed between the first bearing 513a and the second bearing 513b and substantially at the center of the body portion 516.

Each shaft member 520a (520b) has a first end portion 522a (522b), an opposite, second end portion 524a (524b), and a body portion 526a (526b) defined therebetween. The first shaft member 520a and the second shaft member 520b that are received in the first bearing 513a and the second bearing 513b of the bearing member 510, respectively.

The mounting member 560 has a first surface 562, an opposite, second surface 564, a body portion 566 defined therebetween, a shoulder portion 565 extending from the second surface 564, a passage 563 formed through the body portion 566 and the shoulder portion 565, and a first recess 568a and a second recess 568b formed on the first surface 562. The second end 524a of the first shaft member 520a and the second end 524b of the second shaft member 520b are received in and secured to the first recess 568a and the second recess 568b of the mounting member 560, respectively. As assembled, the passage 563 of the mounting member 560 is substantially coaxial with the bore 511 of the bearing member 510.

The collar member 550 has a first surface 552, an opposite, second surface 554, a body portion 556 defined therebetween, and a first recess 558a and a second recess 558b formed on the second surface 554. The body portion 556 of the collar member 550 defines a passage 553 that extends from the center of the first surface 552 to the center of the second surface 554. As assembled, the first end 522a of the first shaft member 520a and the first end 522b of the second shaft member 520b are received in and secured to the first recess 558a and the second recess 558b of the collar member 550, respectively, and the passage 553 of the collar member 550 is substantially coaxial with the bore 511 of the bearing member 510.

The probe 530 has a body portion 532 and a working end portion 534 extending from the body portion 532. The probe 530, in operation, is received in the bore 511 of the bearing member 510 such that the working end portion 534 is substantially coaxial with and extendable through the passage 563 of the mount member 560 to reach the target of interest of the living subject. The probe 530 is driven by a drive mechanism (not shown). The probe 530 can be a surgical drill or other medical devices including brain stimulation means.

In operation, when the drive mechanism drives the probe 530, the bearing member 510 is movable between a first position and a second position accordingly, together with the probe 530, to allow the working end portion 534 to open the access to the target of interest of the living subject and withdraw from the access to the target of interest of the living subject. When the bearing member 510 is moved between a first position and a second position, the bearing member 510 moves slidably along the first shaft 520a and the second shaft 520b between their first ends 522a (522b) and the second ends 524a (524b). Specifically, when the bearing member 510 is moved to the first position, the first end portion 512 of the bearing member 510 is in contact with the second surface 554 of the collar member 550, as shown in FIG. 6. When the bearing member 510 is moved to the second position, the second end portion 514 of the bearing member 510 is in contact with the first surface 562 of the mounting member 560, as shown in FIG. 7. Thus, the working end portion 534 is movable in a range that is determined by the first position and the second position of the bearing member 510, which is corresponding to the space between the second surface 554 of the collar member 550 and the first surface 562 of the mounting member 560.

The platform 540 is adapted for receiving the mounting member 560 and positioning the working end portion 534 of the drill 530 towards the target of interest of the living subject along a planned trajectory so as to provide an access thereto.

The platform 540 includes a base portion 542 and a plurality of supporting legs 544 extending from the base portion 542. The base portion 542 of the platform 540 defines an opening 541 for receiving the shoulder portion 565 of the bearing member 510 therein. Each of the plurality of supporting legs 544 has a length that is different from or substantially identical to each other. For such a platform, when the shoulder portion 565 of the bearing member 510 is received in the base portion 542, the working end portion 534 of the probe 530 is positioned towards the target of interest of the living subject along the planned trajectory. The length of each of the plurality of supporting legs 544 is fixed, or adjustable. The platform 540 can be a customized platform such as a STarFix™ platform where the length of each of three supporting legs is fixed, or a platform as disclosed below in which the length of at least one supporting leg is adjustable, according to one aspect of the present invention.

The STarFix™ platform is custom-made for each patient based on a pre-operative tomogram and the surgeon's identification of the entry point and the target on that tomogram. It is manufactured in a separate manufacturing facility. The platform arrives at the operating room (OR) pre-aimed with no adjustment available intraoperatively.

The present invention, among other things, provides a surgical platform having a plurality of length-adjustable legs with final modifications for each patient accomplished in the OR or in situ. The invented surgical platform has advantages over the current standard platform (such as STarFix™ platform), one of which in particular relates to avoiding the need of sending the preoperatively acquired data and surgical plan for each patient to a separate manufacturing facility to manufacture it, thereby reducing the cost and surgical time, and potential errors. Among many applications, the invented surgical platform can be used in connection with a surgical instrument for providing a percutaneous access to the cochlea of a living subject for performing an otologic surgery and/or to a deep brain of a living subject for performing deep brain stimulation.

To create a surgical platform with a specified surgical instrument (such as a drill) trajectory, a vector needs to be specified. This can be done either by dictating two points or by dictating one point and an angle. As such, several embodiments for the present invention depend upon curved, such as spherical, fiducial markers as these spheres define a plane. Once a plane is specified and defined, two points or one point and an angle in reference to the plane can be generated from individual radiographic images to create the necessary trajectory.

In one embodiment, a surgical platform with adjustable support legs is provided. One support leg is fixed and the other two are adjustable to make the center of the platform concentric with the drill trajectory. The adjustable legs have precisely calibrated scales on them with location for the adjustment specified after analysis of the pre-intervention radiographic images. This provides the entry point for the drill. The angle of entry is made by tilting and rotating the drill with a clamping mechanism known in the art, e.g., a clamping mechanism akin to the IGN product.

In another embodiment, a surgical platform is provided with a rectangular slab sitting on top of one or more fiducial markers. The slab is the same for each patient. To customize this, two points is specified—one on the top and one of the bottom of the slab such that the unique trajectory is achieved. This is done with by printing out labels for the top and bottom or using a laser to etch the proper location. A surgical instrument such as a drill would mount on this with an omni-directional "shoe" such that the drill will pass through both holes.

In yet another embodiment, a surgical platform is provided with divots into rectangular slab. The slab has divots drilled into the bottom of it that correspond to those placed on the patient. The location and depth of these divots is such that the center, vertical axis of the slab is concentric with the drill trajectory. The divots can be formed by a device similar to a plotting printer—instead of a marker a drill would mill to the appropriate depth.

Figure 8:
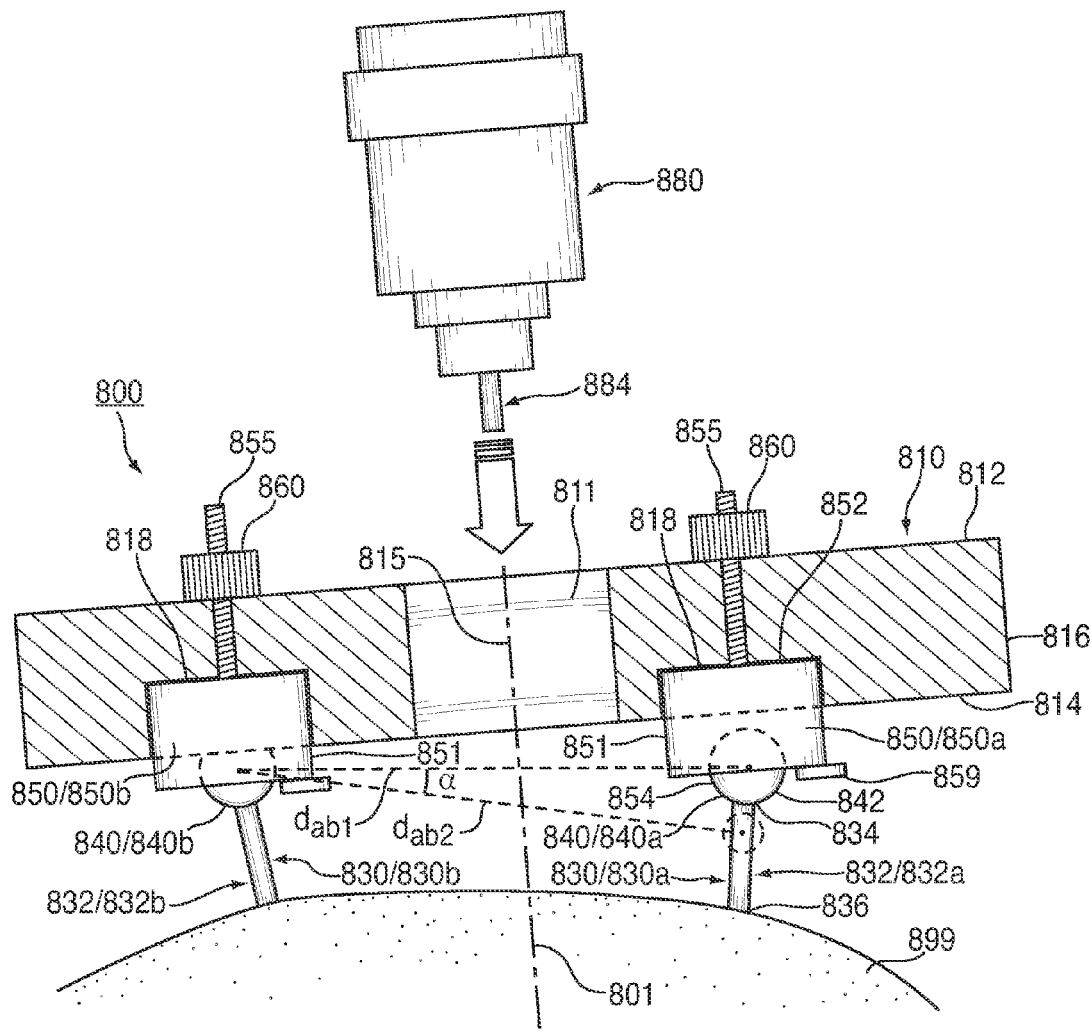
FIG. 8 shows a schematic partial view of a surgical platform according to one embodiment of the present invention.
Figure 9:
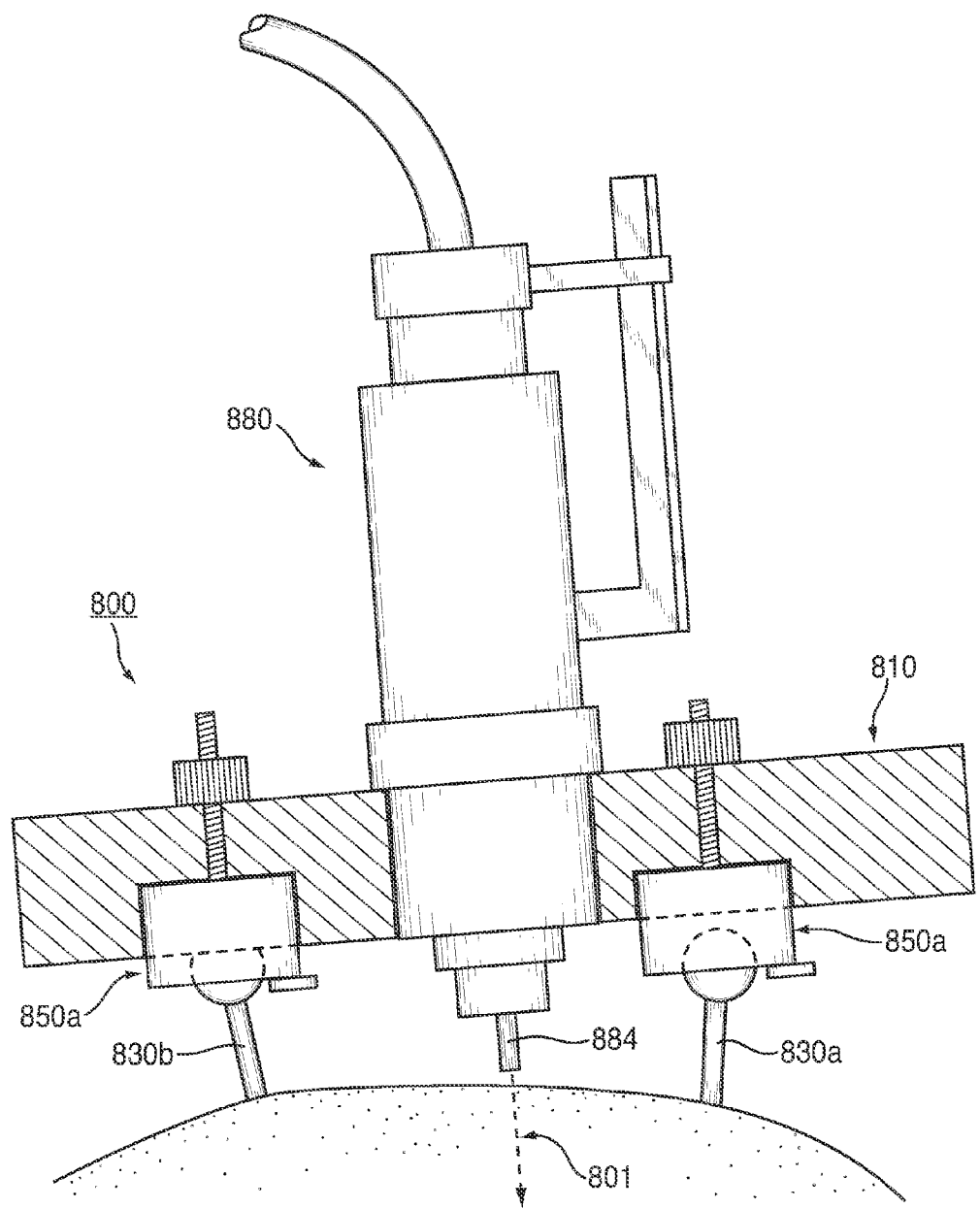
FIG. 9 shows a schematic partial view of the surgical platform shown in FIG. 8.

More specifically, referring now to FIGS. 8-10, in particular, FIG. 8, in one embodiment of the present invention as shown, a surgical platform 800 has a body member 810. The body member 810 has a first surface 812, an opposite, second surface 814, and a body portion 816 defined therebetween, and a plurality of recesses 818 formed on the second surface 814. The body portion 816 defines a bore 811 extending from the first surface 812 to the second surface 814 substantially along a longitudinal axis 815 for receiving a surgical instrument 880. The plurality of recesses 818 is formed such that the recesses 818 have dimensions different from or substantially identical to each other.

Furthermore, the surgical platform 800 has a plurality of mounting members 850. Each mounting member 850 has a body portion 851 defining a concave surface 854, and is received in a corresponding one of the plurality of recesses 818 of the body member 810. The plurality of mounting members 850 may be different from or substantially identical to each other in terms of design and/or dimensions.

In one embodiment, the plurality of mounting members 850 includes a first mounting member 850a, a second mounting member 850b and a third mounting member (not shown). Each of the first mounting member 850a, the second mounting member 850b and the third mounting member has a body portion 851 having a first surface 852 and a second surface 854 that is substantially convex, and a shaft portion 855 extending from the body portion 851 at the first surface 852. The body portion 851 may comprise an at least partially cylindrical body, or an at least partially spherical body. In one embodiment as shown in FIG. 8, each of the first mounting member 850a, the second mounting member 850b and the third mounting member further has an arm member 859 projecting radially away from the second surface 854 of a corresponding body portion 851. The plurality of mounting members 850 is mounted to the body member 810 through the plurality of recesses 818 by an engaging member means 860. In this embodiment, three recesses 818 are formed on the second surface 814 such that each of the three recesses 818 is positioned at a corresponding one of three vertices of a triangle.

Moreover, the surgical platform 800 has a plurality of support members 830. Each support member 830 is engagable with a corresponding one of the plurality of mounting members 850 for supporting the body member 810. In one embodiment, at least one of the plurality of support members 830 is formed with an engagement portion 840 that has a convex surface 842 to be complimentarily received in the concave surface 854 of a corresponding one of the plurality of mounting members 850. Each pair of the plurality of support members 830 defines an adjustable relative position and orientation therebetween. When a relative position and orientation between a pair of the plurality of support members 830 is adjusted, the relative orientation of the longitudinal axis 815 to the planned trajectory 801 is adjusted accordingly.

The plurality of support members 830 can be different from or substantially identical to each other in terms of design and/or dimensions. In one embodiment, the plurality of support members 830 includes a first support member 830a, a second support member 830b and a third support member (not shown). Each of the first support member 830a, the second support member 830b and the third support member includes a shaft portion 832 having a first end portion 834 and an opposite, second end portion 836, an engagement portion 840 mounted to the first end portion 834 of the shaft portion 832, and an end portion (not shown) mounted to the second end portion 836 of the shaft portion 832. The end portion may have a mounting member or magnetic member adapted for engaging a fiducial marker in use. In operation, the end portion is attached onto a region of interest 899 of a living subject in which the surgical procedure is performed.

More specifically, for example, in the embodiment as shown, the shaft portion 832 is formed with an outer threaded segment, and the engagement portion 840 is formed with an outer convex surface 842 and an inner cavity defined by an inner threaded segment (not shown) adapted for movably engaging with the shaft portion 832 through the corresponding outer threaded segment. Accordingly, an effective length of each support member 830 is adjustable by rotating the engagement portion 840 along the shaft portion 832. The relative position and orientation of the first support member 830a to the second support member 830b can be described or characterized by a distance, $d_{ab1}$, defined between the center of the ball member 840a of the first support member 830a and the center of the ball member 840b of the second support member 830b. When the ball member 840a moves along the shaft portion 832 through the thread engagement downward, for example, the center of the ball member 840a moves from a first position to a second position, the distance between the center of the ball member 840a of the first support member 830a and the center of the ball member 840b of the second support member 830b is changed from $d_{ab1}$ to $d_{ab2}$, defining an angle α therebetween. This adjustability in a three-dimensional space allows such a surgical platform to be adjusted in situ for a patient, i.e., a customized surgical platform can be obtained in situ.

In operation, the surgical instrument 880 is engaged with the surgical platform 800 such that a working end portion 884 of the surgical instrument 880 may pass through the bore 811 of the body member 810 and reach the target of interest along the longitudinal axis 815, which is substantially coaxial with a planned trajectory 801. When a relative position and orientation between a pair of the plurality of support members 830 is adjusted, the relative orientation of the longitudinal axis 815 to the planned trajectory 801 is adjusted accordingly. Thus, in other words, one can adjust the relative position(s) and orientation(s) among the plurality of support members to align the longitudinal axis 815 or the working end portion 884 of the surgical instrument 880 to the planned trajectory 801 in situ.

An assembling procedure of the surgical platform 800 according to one embodiment of the present invention is shown in FIG. 10. At first, the body member 810 is provided. A cutting tool 890 is positioned to the body member 810 to define a bore 811 and a plurality of recesses 818 in the body member 810, as shown in FIGS. 10A-10D.

Figure 10A:
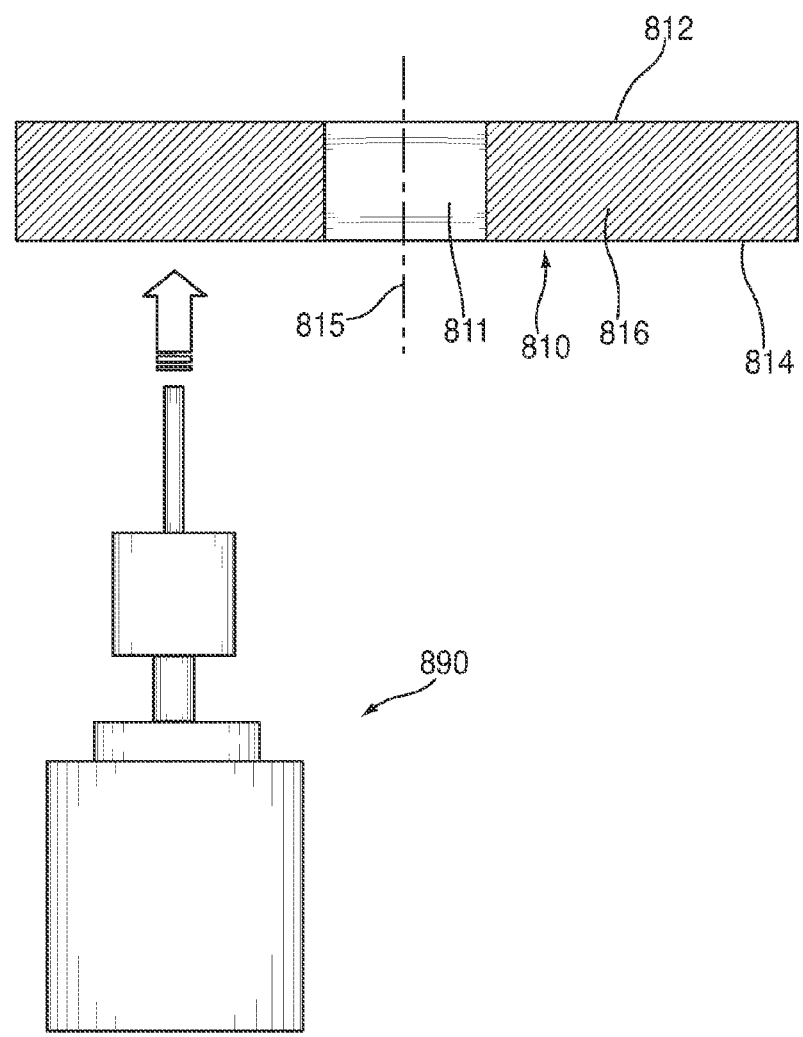
FIGS. 10A-10F show schematic partial views of the surgical platform shown in FIG. 8, respectively, assembled in situ.
Figure 10B:
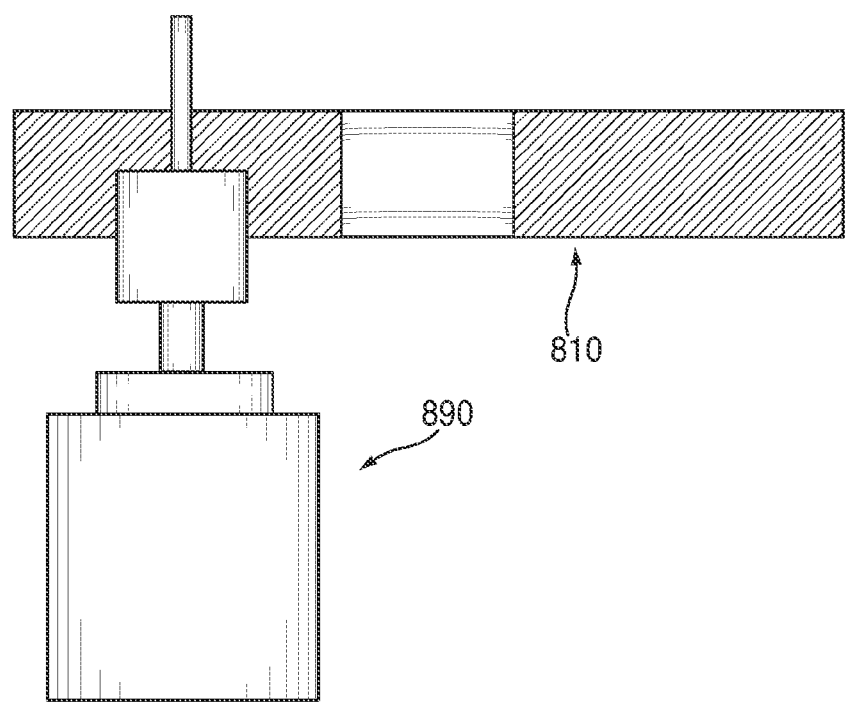
Figure 10C:
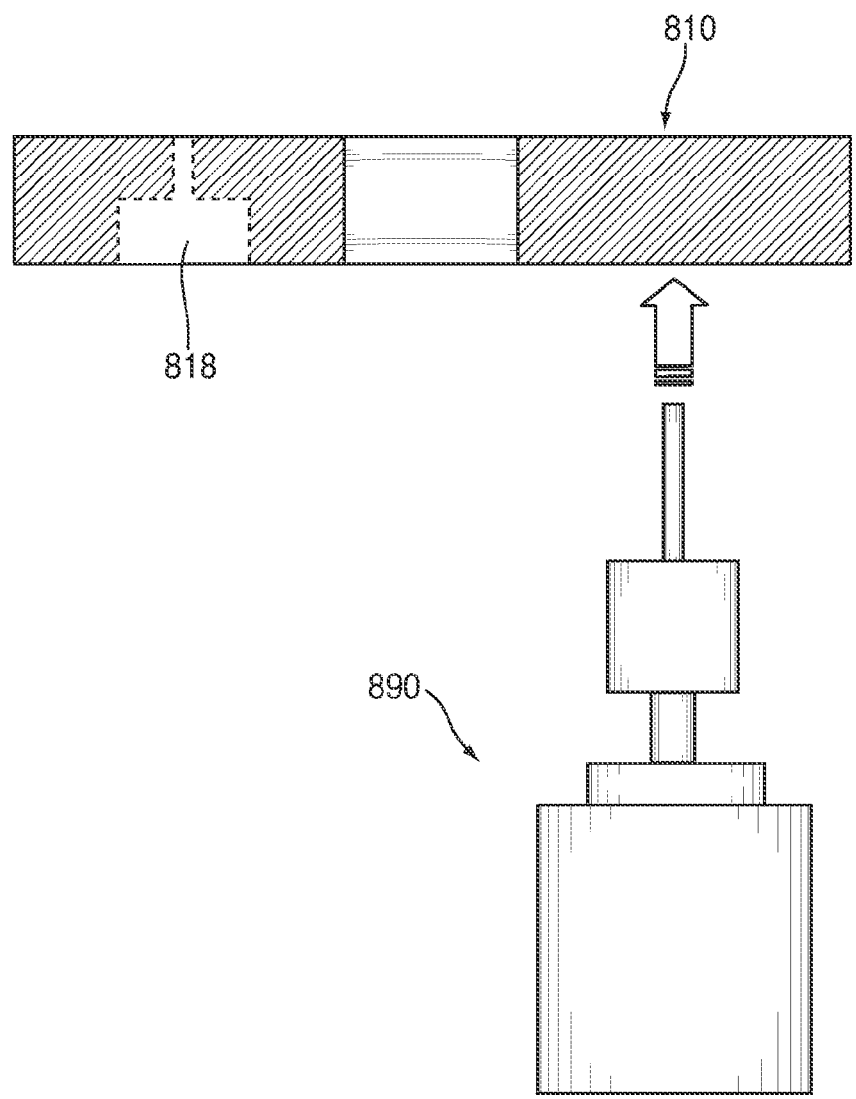
Figure 10D:
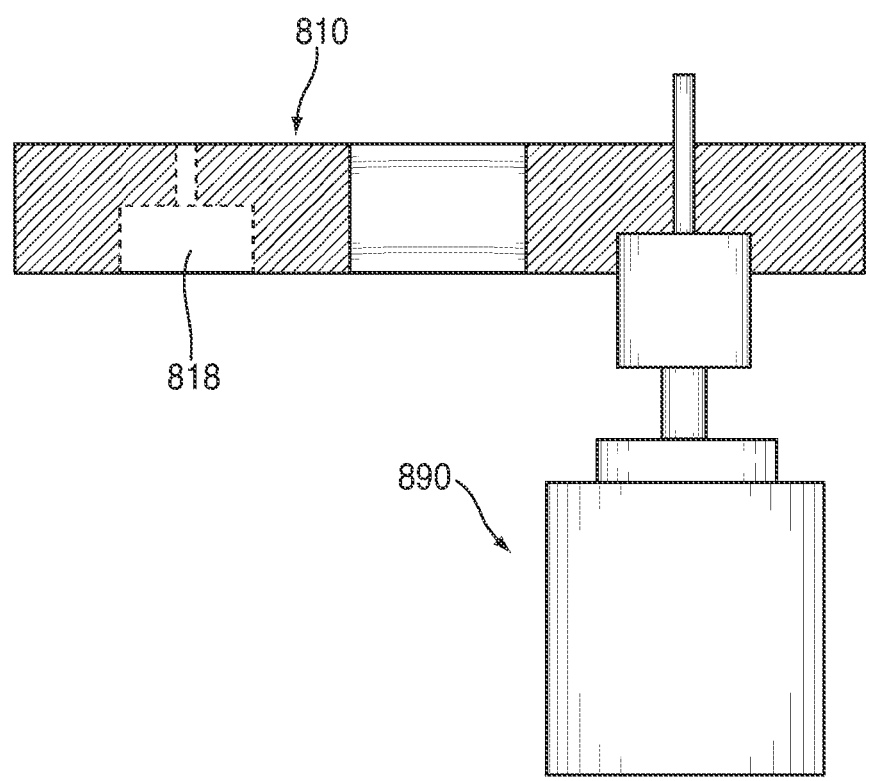
Figure 10E:
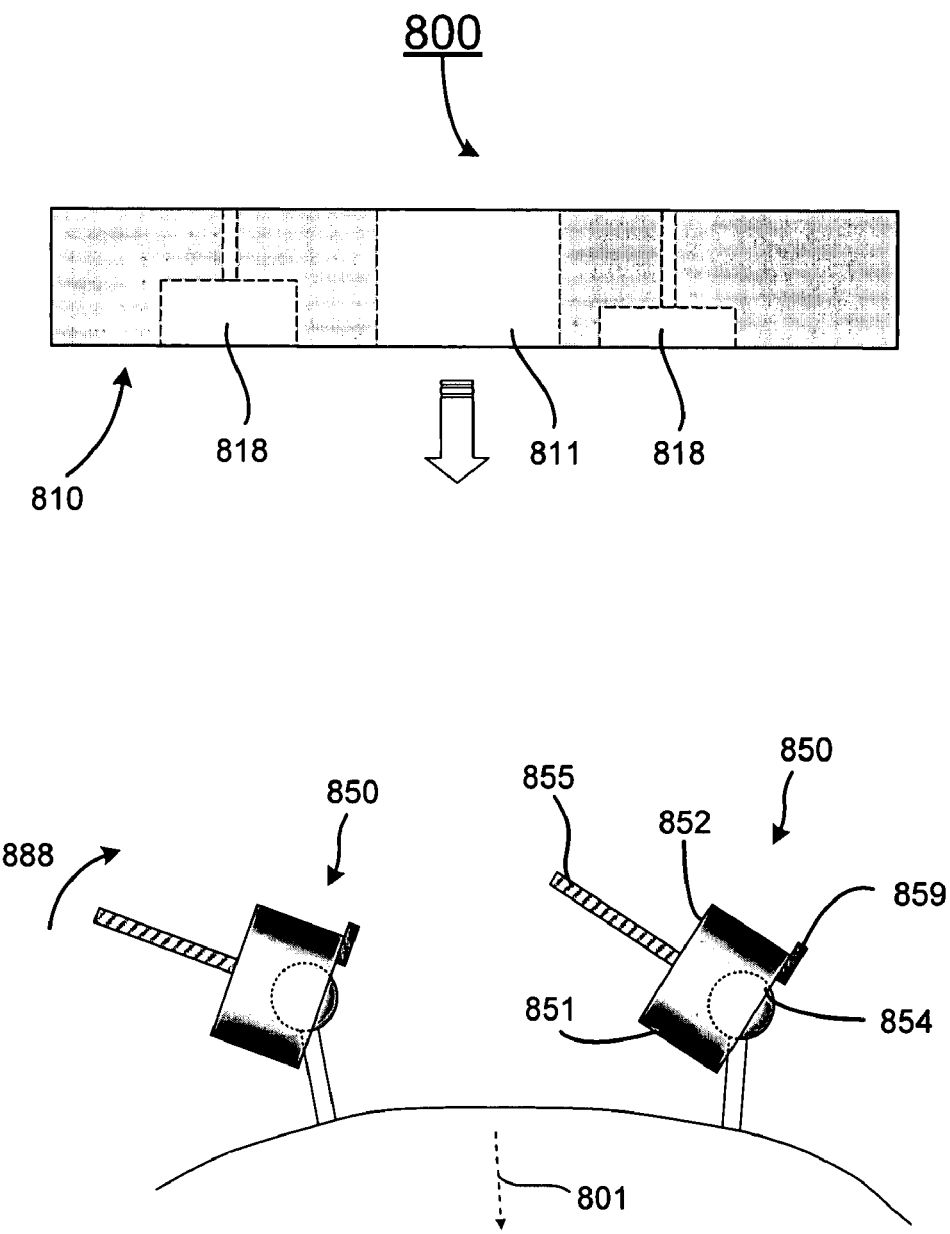

The plurality of mounting member 850 and the plurality of support member 830 are provided. As described above, each mounting member is formed with a concave surface and each support member 830 is formed with a convex (sphere) surface that is substantially complementary to the concave surface of the mounting member 850. Each mounting member 850 is attached to a corresponding support member 830 by engaging the concave surface of the mounting member 850 with the convex surface of the support member 830. Accordingly, each mounting member 850 is rotatable relative to the support member 830 in three dimensions, as shown in FIG. 10E. Additionally, the effective length of each support member 830 is also adjustable, as described above. Therefore, for such an arrangement, the orientation and position of the working end portion of a drill (probe) can be easily aligned to a planned trajectory, by adjusting the effective length of one or more support members 830.

Figure 10F:
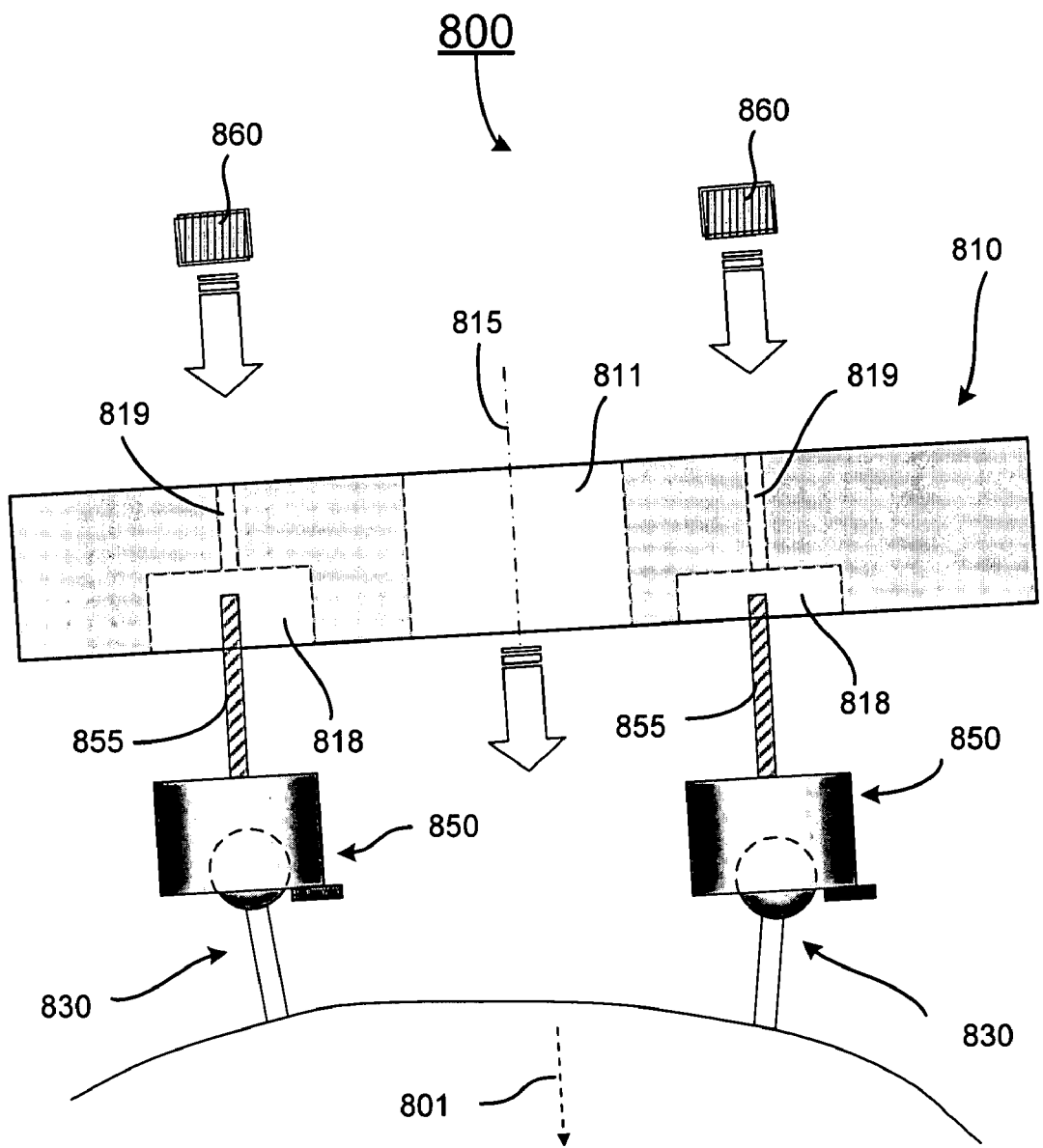

As shown in FIGS. 10E and 10F, each support member 830 in operation, is secured to a region of interest 899 of a living subject in which the surgical procedure is performed. Then each engaged mounting member 850 is placed into a corresponding recess 818 formed in the body member 810, and secured therein by a securing means, such as screws, as shown in 10F.

Figure 11:
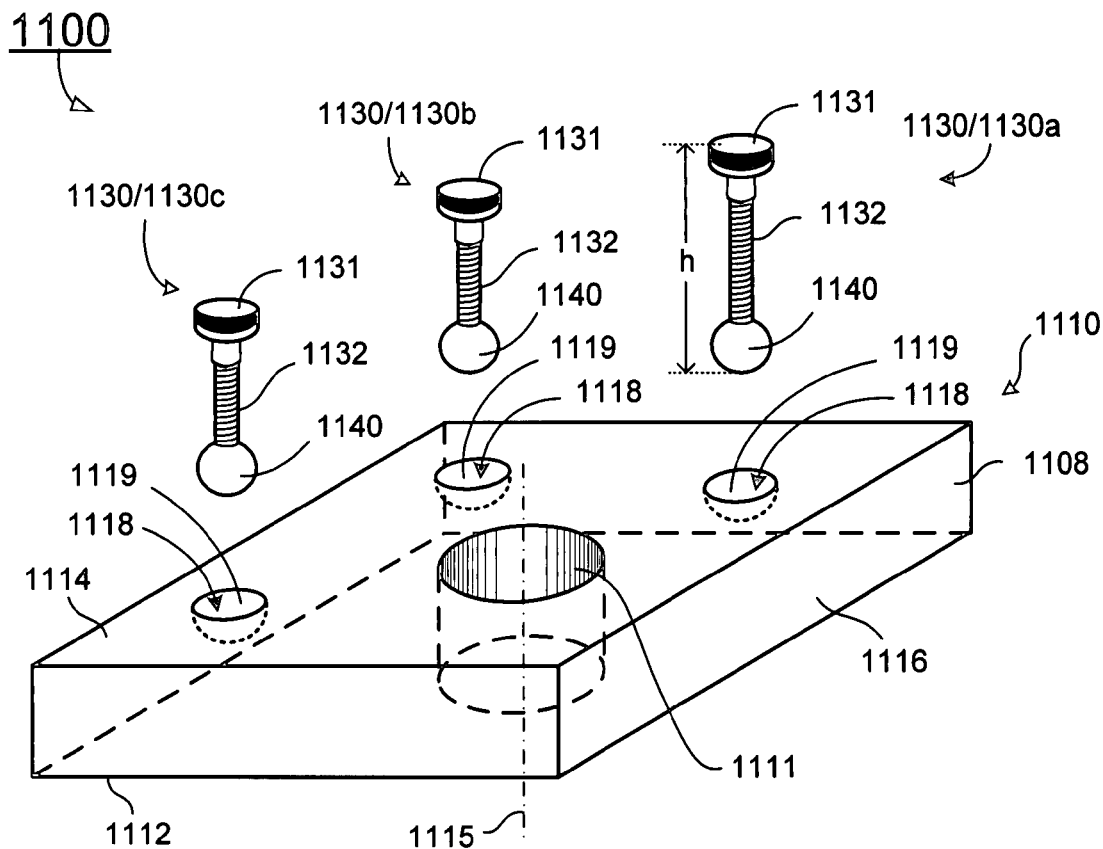
FIG. 11 shows a schematic partial view of a surgical platform according to another embodiment of the present invention.
Figure 12:
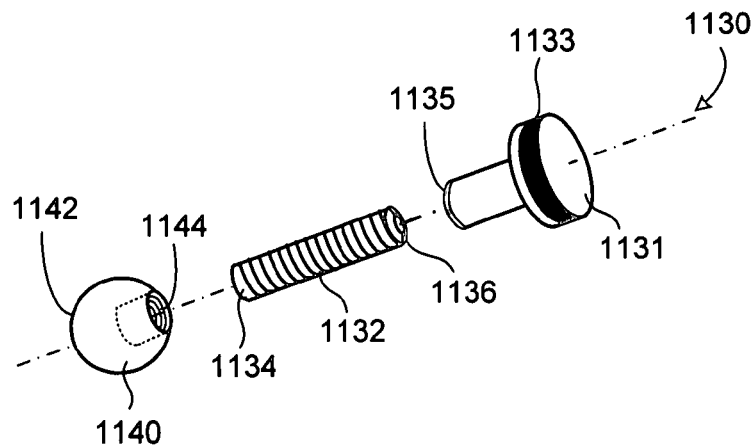
FIG. 12 shows a schematic partial view of a surgical platform shown in FIG. 11.

Referring to FIGS. 11 and 12, and in particular to FIG. 11, a surgical platform 1100 is shown according to another embodiment of the present invention. The surgical platform 1100 is usable for engaging with a surgical instrument as to provide an access to a target of interest of a living subject. The surgical platform 1100 includes a body member 1110 having a first surface 1112, an opposite, second surface 1114, a body portion 1116 defined therebetween, and a plurality of recesses 1118 formed on the second surface 1114. The body portion 1116 defines a bore 1111 extending from the first surface 1112 and the second surface 1114 substantially along a longitudinal axis 1115 for engaging with a surgical instrument (not shown). The surgical platform 1100 also has a plurality of support members 1130. Each support member 1130 is engaged with a corresponding one of the plurality of recesses 1118 of the body member 1110 for supporting the body member 1110.

In one embodiment, at least one of the plurality of recesses 1118 of the body member 1110 is formed with a concave surface 1119. At least one of the plurality of support members 1130 is formed with an engagement portion that has a convex surface 1142 to be received in the concave surface 1119 of the at least one of the plurality of recesses 1118. The convex surface 1142 of the corresponding engagement 1140 of the at least one of the plurality of support members 1130 is substantially complementary to the concave surface 1119 of the at least one of the plurality of recesses 1118.

As such formed, each pair of the plurality of support members 1130 defines an adjustable relative position and orientation therebetween. In operation, the surgical instrument is received in the bore 1111 of the body member 1110 such that a working end portion of the surgical instrument is extendable through the bore 1111 to the target of interest of the living subject along the longitudinal axis 1115, which is substantially coaxial with a planned trajectory 1101.

When a relative position and orientation between a pair of the plurality of support members 1130 is adjusted, the relative orientation of the longitudinal axis 1115 to the planned trajectory 1101 is adjusted accordingly. This adjustability in a three-dimensional space allows such as a surgical platform to be adjusted in situ for a patient, i.e., a customized surgical platform can be obtained in situ.

In the exemplary embodiment, the plurality of support members 1130 has a first support member 1130a, a second support member 1130b and a third support member 1130c. Each of the first support member 1130a, the second support member 1130b and the third support member 1130c comprises a shaft portion 1132 having a first end portion 1134 and an opposite second, end 1136, an engagement portion 1140 mounted to the second end portion 1136 of the shaft portion 1132, and an end portion 1131 mounted to the first end portion 1134 of the shaft portion 1132. The shaft portion 1132 is formed with an outer threaded segment, and the engagement portion 1140 is formed with an outer convex surface 1142 and an inner cavity defined by an inner threaded segment 1144 adapted for movably engaging the shaft portion 1132 through the corresponding outer threaded segment. Therefore, an effective length, h, of the support member 1130 is adjustable by rotating the engagement portion 1140 along the shaft portion 1132. In one embodiment, the engagement portion 1140 includes a ball member and the outer convex surface that is a substantially spherical surface 1142.

In one embodiment, the end portion 1131 comprises a mounting member 1133 adapted for engaging a fiducial marker in use. In another embodiment, the end portion 1131 comprises a magnetic member 1133 adapted for engaging a fiducial marker in use.

The present invention in another aspect relates to a surgical platform has a body member having a first surface, a second, opposite surface, and a body portion defined therebetween, where the body portion defines a bore substantially along a longitudinal axis between the first surface and the second surface, and a plurality of recesses formed on the second surface. The surgical platform also has a plurality of support members, each engagable with a corresponding one of the plurality of recesses, adapted for supporting the body member. At least one of the plurality of recesses is formed with a concave surface and at least one of the plurality of support members is formed with an engagement portion that has a convex surface to be complimentarily received in the concave surface of the at least one of the plurality of recesses. As assembled, each pair of the plurality of support members define an adjustable relative position and orientation therebetween.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A surgical platform usable for engaging with a surgical instrument as to provide an access to a target of interest of a living subject, comprising:
   (a) a body member having a first surface, an opposite, second surface, and a body portion defined therebetween, and a plurality of recesses, wherein each recess is formed with a surface recessed from the second surface and has a socket extending from the recessed surface through the body portion to the first surface, and wherein the body portion defines a bore extending from the first surface to the second surface substantially along a longitudinal axis for receiving the surgical instrument;
   (b) a plurality of mounting members, each mounting member having a body portion having a first surface and a second surface that is substantially concave, and a shaft portion extending from the body portion at the first surface and having a free end portion received in a corresponding one of the plurality of recesses of the body member such that the first surface of the body portion of the mounting member is in contact with the recessed surface of the corresponding recess of the body member and the shaft portion of the mounting member is placed in the socket of the corresponding recess of the body member; and
   (c) a plurality of support members, each support member comprising an engagement portion engaged with a corresponding one of the plurality of mounting members for supporting the body member, wherein the engagement portion of at least one of the plurality of support members is formed with a convex surface to be complimentarily received in the concave surface of a corresponding one of the plurality of mounting members, and wherein each pair of the plurality of support members define an adjustable relative position and orientation therebetween,
   wherein in operation, the surgical instrument is received in the bore of the body member such that a working end portion of the surgical instrument is extendable through the bore to the target of interest of the living subject along the longitudinal axis, which is substantially coaxial with a planned trajectory,
   wherein the plurality of support members comprises a first support member, a second support member and a third support member,
   wherein each of the first support member, the second support member and the third support member further comprises a shaft portion having a first end portion and an opposite, second end portion, and an end portion mounted to the second end portion of the shaft portion, wherein the engagement portion is mounted to the first end portion of the shaft portion,
   wherein the shaft portion is formed with an outer threaded segment, and the engagement portion is formed with an outer convex surface and an inner cavity defined by an inner threaded segment adapted for movably engaging with the shaft portion through the corresponding outer threaded segment, and wherein an effective length of each support member is adjustable by rotating the engagement portion along the shaft portion, such that the angular orientation of the surgical platform is adjustable relative to the target of interest, and
   wherein the surface of at least one recess of the plurality of recesses of the body member is recessed further from the second surface of the body member than the surface of at least one other recess of the plurality of recesses.

2. The surgical platform of claim 1, wherein when a relative position and orientation between a pair of the plurality of support members is adjusted, the relative orientation of the longitudinal axis to the planned trajectory is adjusted accordingly.

3. The surgical platform of claim 1, wherein the engagement portion comprises a ball member and the outer convex surface comprises a substantially spherical surface.

4. The surgical platform of claim 1, wherein the end portion comprises a marker mounting member adapted for engaging a fiducial marker in use.

5. The surgical platform of claim 1, wherein the end portion comprises a magnetic member adapted for engaging a fiducial marker in use.

6. The surgical platform of claim 1, wherein the plurality of mounting members comprise a first mounting member, a second mounting member and a third mounting member.

7. The surgical platform of claim 6, wherein the body portion of each mounting member comprises an at least partially cylindrical body.

8. The surgical platform of claim 6, wherein the body portion of each mounting member comprises an at least partially spherical body.

9. The surgical platform of claim 6, wherein each of the first mounting member, the second mounting member and the third mounting member comprises an arm member projecting radially away from the second surface of a corresponding body portion.

10. The surgical platform of claim 1, further comprising a plurality of engaging member means for mounting the plurality of mounting members to the body member through the plurality of recesses, respectively, wherein each engaging member means is secured to the free end portion of the shaft portion of one of the plurality of mounting members and the first surface of the body member.

11. The surgical platform of claim 1, wherein the plurality of mounting members is different from or substantially identical to each other.

12. The surgical platform of claim 1, wherein the plurality of support members is different from or substantially identical to each other.

13. A surgical platform usable for engaging with a surgical instrument as to provide an access to a target of interest of a living subject, comprising:
 (a) a body member having a first surface, an opposite, second surface, and a body portion defined therebetween, and a plurality of recesses, wherein each recess is formed with a surface recessed from the second surface and has a socket extending from the recessed surface through the body portion to the first surface, and wherein the body portion defines a bore extending from the first surface to the second surface substantially along a first longitudinal axis for receiving the surgical instrument;
 (b) a plurality of mounting members, each mounting member comprising a body portion having a first surface, an opposite, second surface that is substantially concave, and a shaft portion extending from the body portion at the first surface and having a free end portion received in a corresponding one of the plurality of recesses of the body member such that the shaft portion is placed in the socket of the corresponding recess of the body member;
 (c) a plurality of engaging member means for mounting the plurality of mounting members to the body member through the plurality of recesses, respectively, wherein each engaging member means is formed with an inner cavity defined by an inner threaded segment adapted for movably engaging the shaft portion of a corresponding one of the mounting members through the corresponding outer threaded segment such that the position of the body portion of each mounting member, within each corresponding recess along a second longitudinal axis that is substantially parallel to the first longitudinal axis, is adjustable by causing the shaft portion to rotate in relation to a corresponding engaging member means; and
 (d) a plurality of support members for supporting the body member, each support member comprising a shaft portion having a first end portion and an opposite, second end, an engagement portion mounted to the second end portion of the shaft portion, and an end portion mounted to the first end portion of the shaft portion, defining an effective length therewith, wherein the shaft portion is formed with an outer threaded segment and the engagement portion is formed with an inner cavity defined by an inner threaded segment adapted for movably engaging the shaft portion through the corresponding outer threaded segment, and a convex surface that is complimentarily received in the concave surface of a corresponding one of the plurality of mounting members such that each of the mounting members is adjustable relative to a corresponding support member in three dimensions, wherein the effective length of each of the support members is adjustable by rotating the engagement portion of the support member along the shaft portion of the support member, and wherein each pair of the plurality of support members defines an adjustable relative position and orientation therebetween.

* * * * *